United States Patent [19]

Rohrer

[11] Patent Number: 4,641,532
[45] Date of Patent: Feb. 10, 1987

[54] APPARATUS FOR ADJUSTABLY MOUNTING ULTRASONIC TESTING DEVICES

[75] Inventor: Edwin H. Rohrer, Springfield Township, Clark County, Ohio

[73] Assignee: Westinghouse Electric Corp., Pittsburgh, Pa.

[21] Appl. No.: 686,806

[22] Filed: Dec. 27, 1984

[51] Int. Cl.$^4$ .............................................. G01N 29/04
[52] U.S. Cl. .......................................... 73/637; 73/622
[58] Field of Search ................. 73/637, 638, 622, 640

[56] References Cited

U.S. PATENT DOCUMENTS

| | | | |
|---|---|---|---|
| 3,056,286 | 10/1962 | Gibson et al. | 73/622 |
| 3,063,290 | 11/1962 | Kaserman et al. | 73/622 |
| 3,224,254 | 12/1965 | Loving | 73/633 |
| 3,678,735 | 7/1972 | Boulanger et al. | 73/640 |
| 3,828,609 | 8/1974 | Furon et al. | 73/622 |
| 4,099,418 | 7/1978 | Bennett et al. | 73/622 |
| 4,423,636 | 1/1984 | Plante | 73/622 |
| 4,434,660 | 3/1984 | Michaels et al. | 73/622 |

Primary Examiner—Anthony V. Ciarlante

[57] ABSTRACT

Apparatus for adjustably mounting ultrasonic testing devices around a rod end weld for providing water path adjustment to maintain predetermined focal depths of the testing devices, such as transducers. The apparatus enables the transducers to be adjustably radially located with respect to the rod end weld to be tested in order to establish a desirable ultrasonic beam normality. The apparatus provides for the remote actuation thereof.

7 Claims, 6 Drawing Figures

APPARATUS FOR ADJUSTABLY MOUNTING ULTRASONIC TESTING DEVICES

BACKGROUND OF THE INVENTION

1. Technical Field

This invention relates to ultrasonic testing and inspection apparatus for testing and inspecting rod weld ends such as for example the weld joining an end portion to a rod carrying nuclear fuel.

2. Description of the Prior Art

Weld inspection apparatus utilizing manually adjustably transducer mountings may be seen in U.S. Pat. No. 3,056,286 wherein apparatus for inspecting elongated seam welds progressively formed in work moving along a production line is disclosed. The present invention differs patentably from this disclosure in providing for a unique and patentably distinct apparatus for mounting transducers used in ultrasonic testing of rod end welds by providing apparatus that may be remotely actuated with respect to the test area and wherein the apparatus is capable of adjustably positioning the transducer on a plane common with said rod while maintaining a desired focal depth of the transducer signals with respect to the rod end weld being inspected.

U.S. Pat. No. 3,063,290 discloses a system for ultrasonic inspection of tubular objects, such as pipe, wherein the tubular object is rotated on its longitudinal axis is spaced relation to a transducer which is positioned on a dolly which is movable on a parallel path with respect to the tubular object being inspected. The present invention does not incorporate any of the apparatus used in the system of the patent for moving the transducer on a path parallel to the rod end weld being inspected but does provide for adjustment of each of a plurality of transducers individually positioned radially with respect to the area of inspection and on planes common to the longitudinal axis of the rod having the end weld.

U.S. Pat. No. 3,224,254 discloses an ultrasonic inspection apparatus for elongate members wherein the elongate members are moved through the apparatus and the apparatus positioning and holding the transducers are relatively fixed with respect thereto.

The principal novelty in the present invention is the provision of the remotely adjustable means positioning the transducers relative to the rod end weld being tested whereby the transducers supported and adjustably positioned by the apparatus may be moved relative to the rod end weld being tested while maintaining the desired focal depth with respect thereto.

U.S. Pat. No. 3,678,735 discloses an installation for ultrasonic testing of metallic cans and relates to a supply system for maintaining a desirable level of water in a measuring vessel. The system includes emitter-receiver transducers mounted on the side walls of the vessel and focused on the axis of the metallic can passing through the device. The transducers may be manually adjusted for changing the focal distance thereof. There is no disclosure or suggestion of the novel apparatus of the present invention in which the apparatus is remotely actuated and maintains a predetermined focal depth of the transducer with respect to the area of inspection.

U.S. Pat. No. 3,828,609 discloses a tube inspection system comprising an ultrasonic "non-destructive" testing system wherein elongated work pieces such as tubing traveling at high rates of speed are examined by a plurality of transducers positioned along the path of travel of the tubing. The transducers are carried by individual, manually adjustable devices for moving the same on paths parallel to the tubing being examined transversely thereof and circumferentially about an axis spaced with respect to the tubing being inspected.

In the present invention, the apparatus mounting the transducers is both remotely controlled and more importantly capable of moving the transducers on an axis based on the rod end weld so as to maintain a desired focal depth with respect thereto.

U.S. Pat. No. 4,099,418 discloses a system for determining tube eccentricity in which sensors of the ultrasonic type are mounted on movable sensing heads on guide means having rollers engaging the tube moving thereby and supporting it in predetermined spaced relation from the sensors. The sensors are individually, manually adjustable radially of the tube being examined.

The present invention has no comparable structure in the apparatus positioning and adjustably supporting the transducers with respect to the rod weld ends being tested.

The present invention discloses a unique and highly practical apparatus that adjustably mounts ultrasonic testing devices in any desired number of radially and circumferentially spaced relation to a rod weld end to be ultrasonically tested and provides structure adjusting the positioning of said ultrasonic testing devices while maintaining a desired focal depth of each transducer with respect to the weld area being tested.

SUMMARY OF THE INVENTION

Apparatus for adjustably mounting ultrasonic testing devices comprises horizontally and vertically movable supports for positioning an ultrasonic testing device for movement in an arcuate path evenly spaced and on a common plane with respect to a rod having an end weld to be tested. The arcuate path forming a portion of a circle centered on said end weld. The apparatus includes the longitudinal axis of a vertical support tube having a mounting body on its lower end which pivotally supports a housing outwardly thereof having spaced upper and lower plates movably positioning a semi-triangular body in the form of a gear segment, the gear segment being engaged with a worm gear in said housing. Shafts and gears interconnect the worm gear in the housing with a remote manipulating head so that the semi-triangular body may be moved on an arcuate path.

A transducer holder on the semi-triangular body carries a transducer comprising an ultrasonic testing device. The apparatus is adjustably positioned in a test tank into which a rod having an end weld to be inspected is positioned in a predetermined location.

DESCRIPTION OF THE PREFERRED EMBODIMENT

Figure 1:
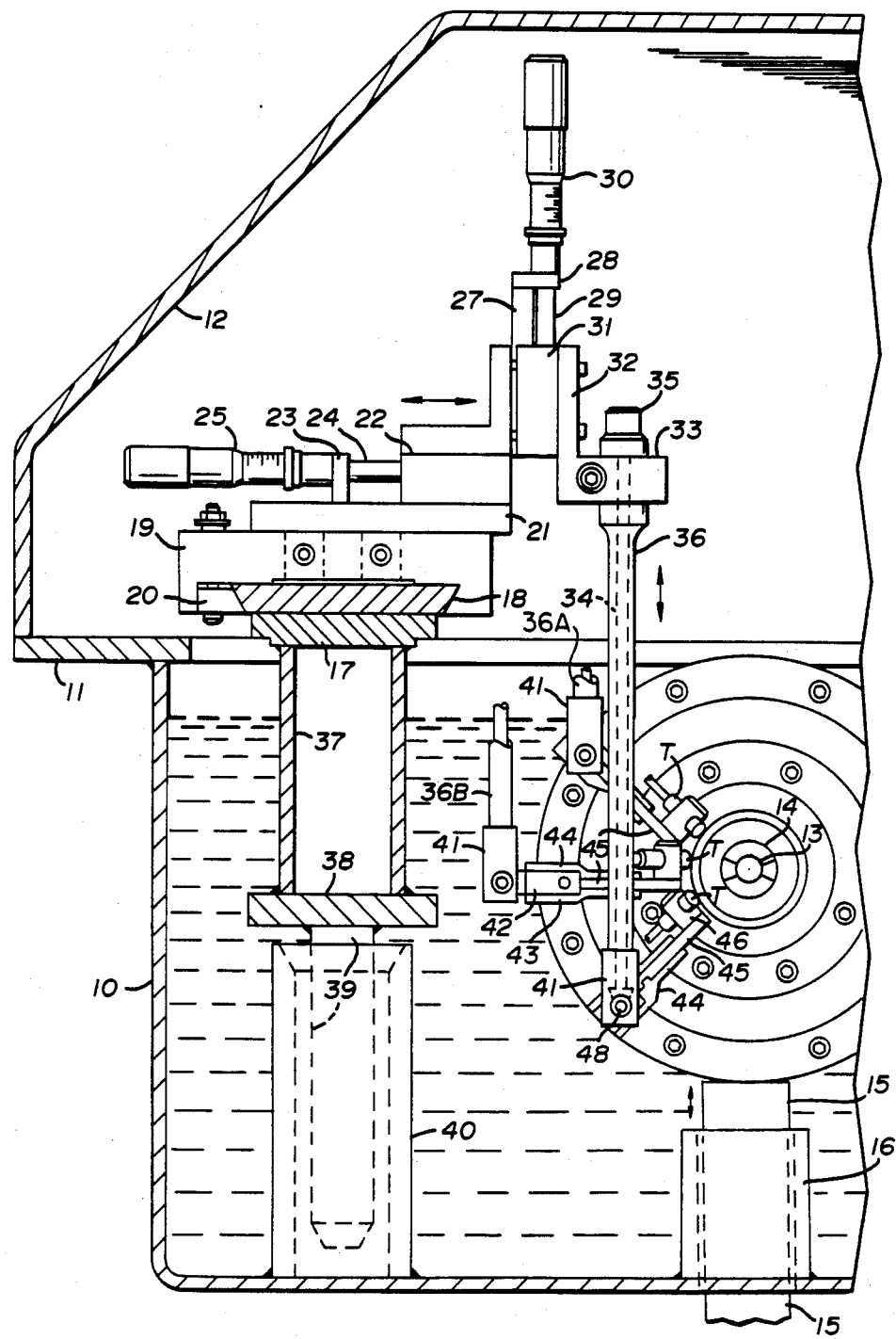
FIG. 1 is a vertical section through a portion of the apparatus for adjustably mounting ultrasonic testing devices showing the same in a test tank.

By referring to the drawings and FIG. 1 in particular, a vertical section through a typical installation of the apparatus for adjustably mounting ultrasonic testing devices may be seen.

In FIG. 1, a test tank 10 is illustrated as having a flat peripheral flange 11 and a removable transparent plastic cover 12 positioned thereover. One of the peripheral walls of the test tank 10 has an aperture 13 therein defined by a movable collet 14. The rod having the end weld to be tested is positioned through the aperture 13 and moved on its longitudinal axis inwardly of the tank 10 to a predetermined point where it engages a vertically movable rod stop member 15 which is located in a cylinder 16 on the bottom of the test tank 10, the vertically movable rod stop extending below the bottom of the test tank 10 and provided with means for moving it vertically.

A suitable gland, not shown, is positioned around the collet 14 on the peripheral wall of the tank 10 so that water in the tank 10 may be maintained at a desirable level.

Still referring to FIG. 1 of the drawings, an inwardly extending member 17 is attached to the peripheral flange 11 and carries a dove-tailed body 18 thereon. A mounting pad slide 19 is movably engaged on the dove-tailed body 18 and secured by a guide block 20. A plate 21 is attached to the dove-tailed body 18 on the upper surface thereof and has a dove-tailed groove formed therein in which a dove-tailed first block 22 is slidably engaged. An upstanding boss 23 on the plate 21 is apertured to rotatably hold a shaft 24 which has a first micrometer head 25 on one side of the boss 23, the other end of the shaft 24 being rotatably caged in the first block 22. The block 22 is L-shaped and on one of its vertical surfaces has a dove-tailed slot which slidably receives a vertically movable body member 31. A second block 27 extends upwardly from the first block 22 and has a horizontally disposed boss 28 on its upper end which is apertured to rotatably hold a shaft 29 to which a second micrometer head 30 is attached. The vertically movable body member 31 cages a configuration on the lower end of the shaft 29 so that the body member 31 is movable vertically responsive to rotation of the second micrometer head 30. A third block 32, which is also L-shaped, is attached to the vertically movable body member 31 and a horizontal portion 33 thereof is apertured to receive a manipulating shaft 34, the upper end of which is engaged in a head 35. A support tube 36 is attached to the lower surface of the horizontal portion 33 of the third block 32 and depends therefrom and encloses the manipulating shaft 34. It will thus be seen that the support tube 36 may be moved toward and away from the peripheral wall of the tank 10 in which the movable collet 14 is positioned as occurs when the mounting pad slide 19 is moved relative to the dove-tailed body 18. It will also be seen that the support tube 36 may be moved toward and away from the peripheral wall of the test tank 10 as seen in the left of FIG. 1 as occurs when the first micrometer head 25 is rotated and the first block 22, the second block 27, the vertically movable body member 31 and the third block 32 move responsive thereto. The horizontal and vertical motion imparting elements comprise a first support means.

It will also be seen that the support tube 36 may be moved vertically by rotary motion imparted the second micrometer head 30 which results in the vertical movement of the vertically movable body member 31 and the third block 32 which directly supports the support tube 36.

In a typical grouping of the apparatus for adjustably mounting ultrasonic testing devices, a number of these assemblies for imparting horizontal motion and vertical motion to the support tube 36 are employed.

In FIG. 1 of the drawings, portions of two additional support tubes 36A and 36B will be seen and it will be understood that each of these additional support tubes 36A and 36B has a complete assembly of the horizontal and vertical motion imparting devices as hereinbefore described in connection with the support and motion imparted the support tube 36.

Additionally, in a typical testing apparatus formed in accordance with this invention, an oppositely disposed group of the apparatus for adjustably mounting ultrasonic testing devices are positioned on the right side of the collet 14 so that at least six transducers may be positioned radially around the rod end weld when the rod is positioned in the collet 14 as hereinbefore described.

Figure 6:
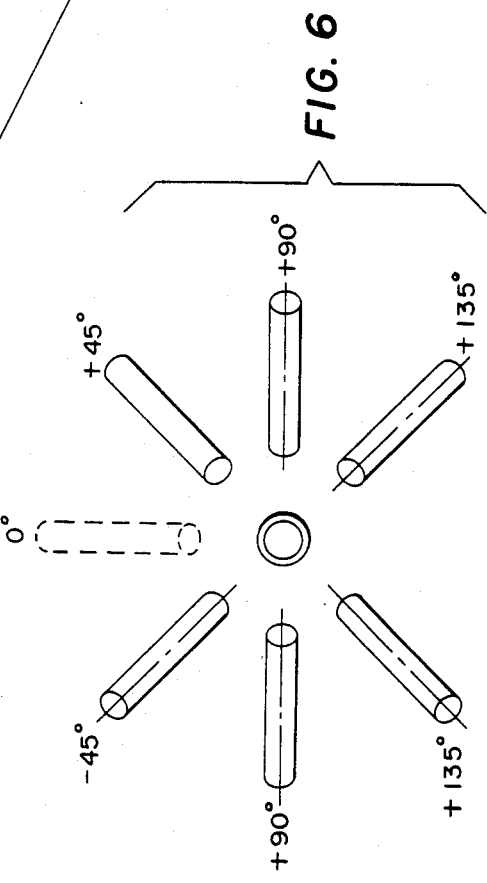
FIG. 6 is a diagrammatic illustration of a plurality of ultrasonic testing devices positioned relative to a rod end weld to be inspected and made possible by utilizing the device of the invention.

It will occur to those skilled in the art that it is possible and frequently desirable to mount an additional horizontal and vertically movable support tube carrying another apparatus for adjustably mounting an ultrasonic testing device and wherein the device would be positioned directly above the rod end weld to be tested as shown in the diagrammatic FIG. 6 of the drawings by positioning another typical group of the horizontal and vertical motion imparting elements on a member extending inwardly of the peripheral flange 11 of the test tank 10 on the side thereof oppositely disposed with respect to the peripheral wall in which the collet 14 is positioned.

Still referring to FIG. 1 of the drawings, it will be seen that a typical group of the motion imparting elements hereinbefore referred to and in particular the inwardly extending member 17 is provided on its lowermost surface with a tubular member 37 which is provided with a bottom portion 38 and from which a guide pin 39 depends for registry with a cylindrical guide 40 positioned on the bottom of the test tank 10.

Preferably, two of these guide assemblies are provided for all of the horizontal and vertical motion imparting groups, such as hereinbefore described and illustrated in FIG. 1 of the drawings.

Those skilled in the art will observe that the transducers T hereinbefore referred to and which are most advantageously positioned by the apparatus for adjustably mounting the same, comprise transducers which serve as a transmitter receiver and may include a piezo electric crystal (lithium sulphate, quartz, etc.) that operates to convert electrical shock energy into mechanical vibrations at a very high, ultrasonic frequency. In such an arrangement, transmitting time is in the order of one microsecond and with a much longer interval for listening. The transducers are positioned with respect to the rod end weld under inspection so that the waves therefrom will strike the weld area. The sound waves comprising the mechanical vibrations penetrate the weld area and are refracted since the weld acts as a conducting medium for sound. When the sound wave from the transducer initially contacts the weld area, a portion of the sound wave is reflected from the weld area back to the transducer and the echo is displayed on an oscilloscope. When there is no flaw in the weld area there will be no other reflection therefrom. However, if there is a flaw in the weld area, the wave will contact the interface of the flaw and will be reflected back to the transducer which in turn transmits the flaw indicating signal to the oscilloscope.

Those skilled in the art will observe that such ultrasonic testing is preferably performed while the rod having the weld area being tested is slowly revolved on its longitudinal axis.

In the present invention, means is provided for slowly rotating the collet 14 to impart such rotary motion to the rod. Such rotation may be started responsive to the rod being positioned through the collet 14 and engaged against the vertically movable rod stop 15 and such engagement used to actuate the means revolving the rod and for retracting the vertically movable rod stop 15 to a position substantially below the rod and the weld area thereof to be inspected.

Still referring to FIG. 1 of the drawings, it will be seen that the support tube 36 has a mounting body 41 on its lowermost end which pivotally supports a housing 42 which is provided with upper and lower plates 43 and 44 respectively, which in turn position a semi-triangular body 45 which carries a transducer holder 46 on its outer end. Each of the additional support tubes 36A and 36B, as seen in FIG. 1 of the drawings, carries a duplicate assembly of the last mentioned elements. The semi-triangular body 45 being positioned on a plane common with the longitudinal axis of the rod having the end weld to be tested. The mounting body 41, housing 42 and plates 43–44 comprise a second support means and the semi-triangular body 45 comprises a third support means.

Figure 2:
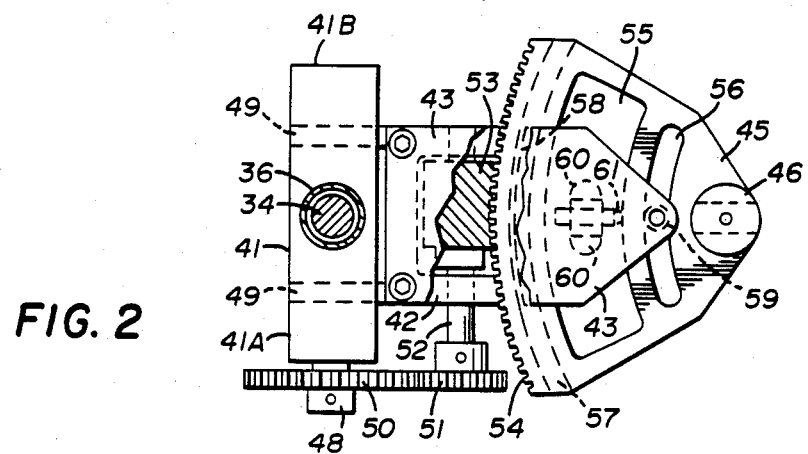
FIG. 2 is an enlarged top plan view with parts broken away and parts in cross section illustrating one of the support tubes, mounting body, housing, and semi-triangular body used in positioning one of the ultrasonic testing devices seen in FIG. 1.
Figure 3:
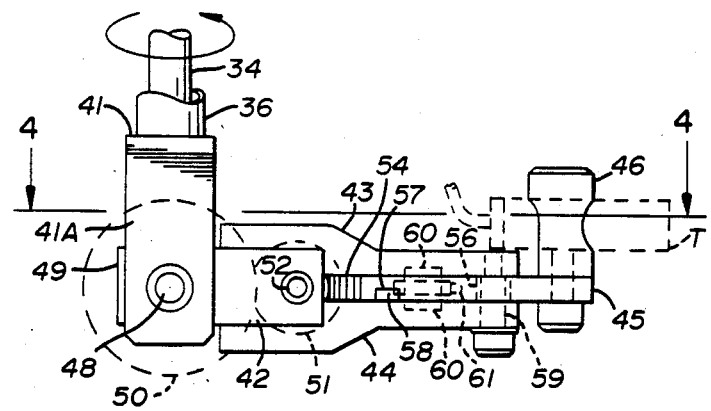
FIG. 3 is a side elevation of the apparatus illustrated in FIG. 2 and includes a broken line representation of an ultrasonic testing device.
Figure 4:
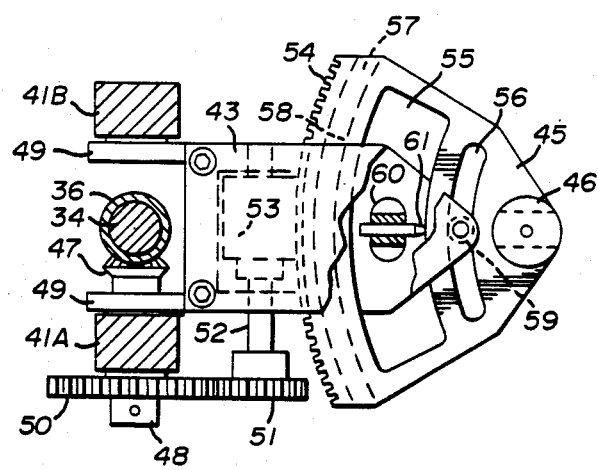
FIG. 4 is a horizontal section on line 4—4 of FIG. 3.

By referring now to FIGS. 2, 3 and 4 of the drawings, enlarged top plan, side and horizontal sectional elevations of the apparatus on the lower ends of the support tube 36 may be seen and by referring thereto the mounting body 41 on the lower end of the support tube 36 will be seen to be of an inverted U-shape with the depending portions 41A and 41B being spaced horizontally with respect to the lower end of the manipulating shaft 34 which extends downwardly therebetween and carries a first beveled gear 35 on its lowermost end. The beveled gear 35 engages a right angularly disposed second beveled gear 47 which is mounted on the end of a rotatable shaft 48 which extends through an aperture in the depending portion 41A of the mounting body 41, the shaft 48 also extending through an aperture in one of a pair of arms 49 which extend in spaced relation from the housing 42 hereinbefore described. A first gear 50 on the other end of the rotatable shaft 48 engages the second gear 51 on a shaft 52 which is rotatably positioned in an aperture in the side wall of the housing 42 and engaged on a worm gear 53. The worm gear 53 is positioned for continuous engagement with gear teeth 54 on an arcuate portion of the semi-triangular body 45. The semi-triangular body 45 has a wide arcuate slot 55 extending transversely thereof and guide configurations comprising a narrow arcuate slot 56 spaced outwardly from the wide arcuate slot 55 and an arcuate groove 57 spaced inwardly from wide arcuate slot 45, the slot 56 and groove 57 also extending transversely of the semi-triangular body 45.

The arcuate groove 57 is located in the lower surface of the semi-triangular body 45 and adjacent the gear teeth 54 and registers with a shorter arcuate rib 58 formed on the upper surface of the lower plate 44. A follower pin 59 is secured at its ends to the upper and lower plates 43 and 44 respectively and is of a diameter that slidably fits the narrow arcuate slot 56 in the semi-triangular body 45. It will thus be seen that rotation of the worm gear 53 by motion originated by revolving the head 35 as seen in FIG. 1 of the drawings, will cause the semi-triangular body 45 to move on an arcuate path and that a transducer T as shown in FIG. 3 of the drawings in broken lines positioned in the transducer holder 46 on the semi-triangular body 45, will move on an arcuate path on a common plane with the longitudinal axis of the rod having the rod end weld to be inspected and spaced radially with respect thereto thus enabling the transducer T to be positioned with its focal depth trained on the weld area to be tested.

It will further be observed that by rotating the head 35, which comprises the point of remote actuation control in the disclosed apparatus, the transducer T may be moved along the rod on an arc so spaced from the rod end weld being inspected as to maintain the same focal depth when the angle of the water path transmission is changed with respect to the longitudinal axis of the rod and the rod end weld. The apparatus thus maintains the critical spacing of the transducers with respect to the weld so as to pick up the maximum frequency response and thus insure the accuracy of the test.

Still referring to FIGS. 2, 3, and 4 of the drawings, it will be seen that oppositely disposed recesses 60 in the upper and lower plates 33 and 34 position a detent plunger 61 for tensioned engagement against one of the arcuate walls defining the wide slot 55 in the semi-triangular body 45. Detents in this wall enable the detent plunger 61 to register with preset locations determining the angular disposition of the transducer carried by the device with respect to the rod and the rod end weld to be tested.

Figure 5:
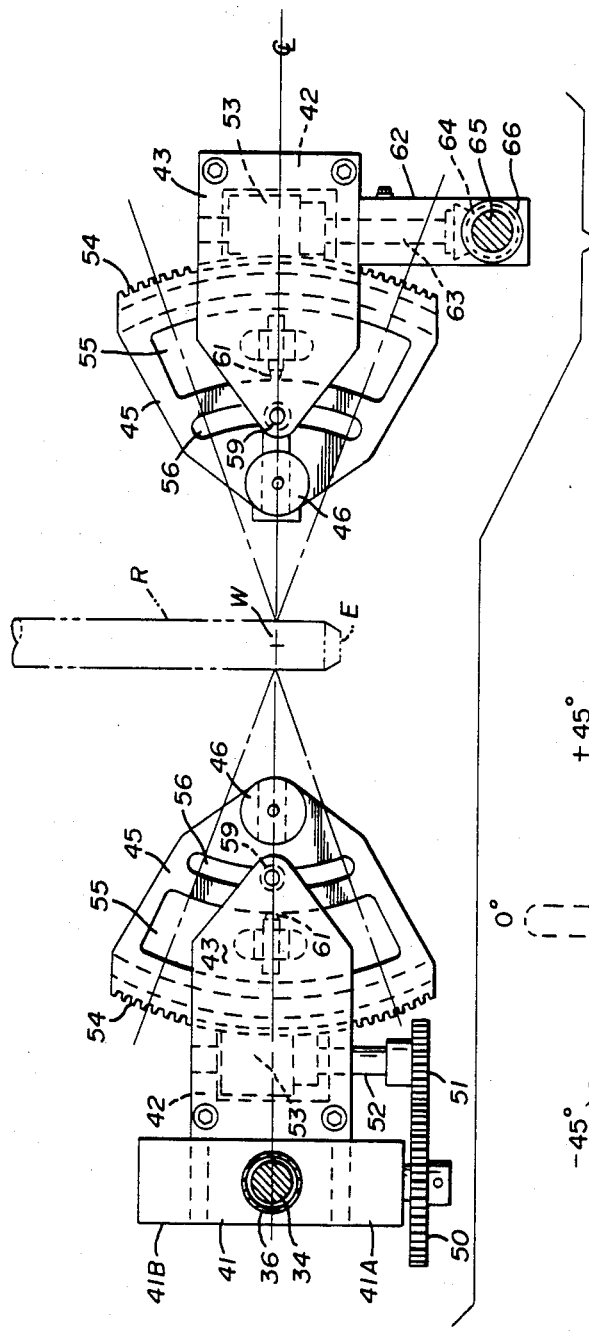
FIG. 5 is a composite view of a horizontal section of two of the devices of the invention positioned on the opposite sides of a rod having end welds to be inspected.

By referring now to FIG. 5 of the drawings, a top plan view with parts in cross section will be seen to illustrate a pair of oppositely disposed apparatus, each of which will hold a transducer in remotely adjustable relation to a broken line representation of a rod R and a weld area W thereon to be tested, the weld area W being inwardly of a beveled end E.

In FIG. 5 of the drawings, the left hand apparatus includes the mounting body 41 carried on the lower end of the support tube 36 which encloses the manipulating shaft 34 as hereinbefore described. The apparatus in the right hand portion of FIG. 5 illustrates an alternate mounting of the housing 42 and the upper and lower plates 43 in that a secondary mounting body 62 is adjustably attached to the housing 42 and an elongated shaft 63 replaces the shaft 52 which carries the worm gear 53 as hereinbefore disclosed.

Secondary right angular beveled gears 64 are positioned on an end of the shaft 63 and a secondary manipulating shaft 65 which secondary manipulating shaft 65 extends upwardly through a support tube 66 which is therefore offset sidewardly with respect to the axis of the housing 42 and the upper and lower plates 43 and 44 which position the semi-triangular body 45.

In FIG. 5 of the drawings, a center line extends through the oppositely disposed apparatus for adjustably mounting transducers which comprise the ultrasonic testing devices and lines above and below the center line and positioned at 35 degrees with respect thereto and terminating at the surface of the weld W to be examined indicate optional positions in which the transducers may be positioned so as to provide for axial or para-axial shear wave direction.

It will be seen that the devices hereinbefore described for imparting horizontal and vertical motion to the support tubes which carry the apparatus for adjustably mounting the ultrasonic testing devices such as the transducers T, enable the water path of the transducer signals and reflections thereof to be directed at the beveled ends of the rods which are preferably beveled at 45 degrees from the lontitudinal axis of the rod and that the same adjustment capability, all of which is remotely actuated with respect to the rod end weld, the rod, or the beveled end thereof, enables the rod end, the bevel and the weld area, to be tested from any desired position.

It will thus be seen that an apparatus for ajustably mounting ultrasonic testing devices such as transducers with respect to a rod having a rod end weld to be tested has been disclosed which provides a relatively easy and fast adjustment while maintaining the focal depth of the ultrasonic testing devices with respect to the area tested.

Although but one embodiment of the present invention has been illustrated and described, it will be apparent to those skilled in the art that various changes and modifications may be made therein without departing from the spirit of the invention and having thus described my invention, what I claim is:

1. An improvement in apparatus for adjustably mounting an ultrasonic testing device in an ultrasonic tester having an open top container with an opening in a peripheral wall thereof, means in said opening for positioning a rod having a weld area to be tested in said container, first support means mounted on said container and extending over and depending into said container and movable horizontally and vertically; the improvement comprising adjustable second support means on said first support means forming an arcuate path on a portion of a circle centered on said weld area of said rod and on a common plane with said rod and third support means positioning said ultrasonic testing device on said arcuate path whereby the focal depth of said ultrasonic testing device is uniformly focused on said weld area to be tested when said third support means and said ultrasonic testing device thereon are moved on said arcuate path and liquid in said container at a predetermined elevation.

2. The improvement in the apparatus for adjustably mounting an ultrasonic testing device in an ultrasonic tester set forth in claim 1 and wherein said first support means include a vertically positioned support tube, a manipulating shaft positioned axially of said support tube and means on one end of said manipulating shaft for imparting rotary motion thereto and wherein said second support means includes a mounting body on one end of said support tube, a housing movably attached to said mounting body and extending sidewardly therefrom, a bifurcated member on said housing extending outwardly therefrom, a gear segment having an arcuate slot and an arcuate groove therein movably positioned in said bifurcated member, body members on said bifurcated member engaging said arcuate slot and said arcuate groove in said gear segment, a worm gear in said housing engaged on said gear segment and a plurality of shafts and gears interconnecting said worm gear and said manipulating shaft and wherein said ultrasonic testing device is positioned on said gear segment whereby rotary motion imparted said manipulating shaft moves said gear segment and said ultrasonic testing device on said arcuate path with respect to said rod and said weld area.

3. The improvement in apparatus for adjustably mounting an ultrasonic testing device in an ultrasonic tester set forth in claim 1 and wherein a stop member is positioned in said open top container for movement from a first position below said rod having a weld area to be tested in said container to a second position engageable by said rod to be tested in said container whereby the rod having a weld area to be tested is positioned in a predetermined location with respect to said ultrasonic testing device.

4. The improvement in apparatus for adjustably mounting an ultrasonic testing device in an ultrasonic tester set forth in claim 1 and wherein said means in said opening for positioning a rod having a weld area to be tested comprises a collet rotatably positioned in said opening in said peripheral wall and means for imparting rotary motion to said collet.

5. The improvement in apparatus for adjustably mounting an ultrasonic testing device in an ultrasonic tester set forth in claim 1 and wherein said second support means on said first support means comprises a mounting body, a housing pivotally engaged on said mounting body, spaced plates extending from said housing on said common plane with said rod having a weld area and a gear segment partially positioned between said spaced plates and movable in its entirety on said arcuate path transversely of said spaced plates, a portion of said gear segment extending outwardly of said spaced plates in oppositely disposed relation to said housing and means on said portion of said gear segment extending outwardly of said spaced plates for mounting said ultrasonic testing device.

6. An improvement in apparatus for adjustably mounting an ultrasonic testing device in an ultrasonic tester having an open top container with an opening in a peripheral wall thereof, means in said opening for holding an elongated object to be tested inwardly thereof, first support means mounted on said container extending over and depending into said container and movable horizontally and vertically, the improvement comprising a mounting body on said first support means, a housing including hinge elements pivotally connected to said mounting body, spaced plates extending from said housing, a semi-triangular flat body movably positioned partially between said spaced plates on a common plane with said elongated object to be tested, configuration in said flat body defining an arcuate path transversely thereof and on said common plane, said arcuate path forming a portion of a circle centered on said elongated object, means on said spaced plates slidably engaging said configurations, an arcuate peripheral edge on said flat body, drive means in said housing engaging said arcuate peripheral edge to move said semi-triangular flat body on said arcuate path, manipulating members extending between said first support means and said drive means engaging said arcuate peripheral edge of said semi-triangular flat body to transmit motion thereto and means on said semi-triangular flat body holding said ultrasonic testing device whereby motion imparted said manipulating members moves said semi-triangular flat body and the ultrasonic testing device thereon on said arcuate path with respect to said elongated object and on said common plane and liquid in said container at a predetermined level.

7. An improvement in apparatus for adjustably mounting an ultrasonic testing device in an ultrasonic tester for rod end welds, said apparatus having an open top container with an opening formed in a wall thereof, a collet in said opening for holdling a rod having an end weld to be tested in said container, first support means mounted on said container and extending into said container and movable horizontally and vertically; the improvement comprising second support means on said first support means positioned in spaced parallel relation to said rod having an end weld to be tested and forming an arcuate path on a plane common with said rod, said arcuate path being a portion of a circle centered on said end weld, said ultrasonic testing device positioned on said arcuate path, said ultrasonic testing device having a known focal depth whereby said focal depth of said ultrasonic testing device is uniformally focused on said end weld when said ultrasonic testing device is moved on said arcuate path, and liquid in said container at a predetermined elevation.

* * * * *